United States Patent [19]

Khanna et al.

[11] Patent Number: 5,410,044
[45] Date of Patent: Apr. 25, 1995

[54] PROCESS FOR PREPARING Z AND E-ROTAMERS OF 3-HYDROXY CEPHEM DERIVATIVES

[75] Inventors: Jag M. Khanna; Yatendra Kumar; Arun Malhotra; Rakesh Arora; Neera Tiwari, all of New Delhi, India

[73] Assignee: Ranbaxy Laboratories, Ltd., New Delhi, India

[21] Appl. No.: 19,269

[22] Filed: Feb. 18, 1993

[30] Foreign Application Priority Data

Aug. 10, 1992 [IN] India ............... 700/DEL/92

[51] Int. Cl.$^6$ ............................ C07D 501/04
[52] U.S. Cl. ....................... 540/222; 540/221
[58] Field of Search ............ 540/222, 221; 514/202

[56] References Cited

U.S. PATENT DOCUMENTS

| | | | |
|---|---|---|---|
| 3,917,587 | 11/1975 | Chauvette | 260/243 C |
| 4,031,084 | 6/1977 | Kukolja et al. | 260/243 C |
| 4,389,524 | 6/1983 | Scartazzini et al. | 544/16 |
| 4,477,658 | 10/1984 | Scartazzini et al. | 544/16 |
| 4,591,642 | 5/1986 | Scartazzini et al. | 544/16 |
| 4,668,781 | 5/1987 | Scartazzini et al. | 540/215 |

Primary Examiner—Nicholas Rizzo
Attorney, Agent, or Firm—Meltzer, Lippe, Goldstein, Wolf, Schlissel & Sazer

[57] ABSTRACT

A process for the manufacture of 7-acylamino-3-hydroxycephem-4-carboxylate-1-oxide in E-rotamer form (Formula III), comprises reacting a 7-acylamino-3-exomethylenecepham-4-carboxylate-1-oxide with ozone in an inert organic solvent in the presence of a catalytic amount of an organic or inorganic base at a temperature ranging from about −80° C. to about +20° C. The E-rotamer (wherein the 3-hydroxy group is strongly hydrogen bonded to the carbonyl of the 4-ester group) exhibits different chemical and physical properties from and is more thermodynamically stable than, the Z-rotamer (wherein there is no hydrogen bonding between the 3-hydroxy group and the carbonyl of the 4-ester group).

18 Claims, 4 Drawing Sheets

PROCESS FOR PREPARING Z AND E-ROTAMERS OF 3-HYDROXY CEPHEM DERIVATIVES

BACKGROUND OF THE INVENTION

Cephalosporins like Cefaclor, Cefroxadine, Ceftizoxime, Ceftibuten, etc., are clinically useful antibiotics. The manufacturing process for these drugs involves multiple steps and hazardous chemicals, and poses many environmental problems. One of the key intermediates used in the manufacture of these cephalosporin antibiotics is 7-acylamino-3-hydroxy-cephem-1-oxide-4-carboxylic acid esters.

The synthesis of 7-acylamino-3-hydroxy-cephem-4-carboxylate-1-oxide was reported earlier by Scartazzini et al. in U.S. Pat. Nos. 4,389,524 (June 1983); 4,447,658 (October 1984), 4,591,642 (May 1986); and 4,668,781 (May 1987), and by Kukolja et al. in U.S. Pat. Nos. 3,917,587 (November 1975) and 4,031,084 (June 1977) through the ozonolysis of 7-acylamino-3-exomethylene-cepham-4-carboxylate and corresponding 1-oxides. Scartazzini et al. have greatly emphasized the formation of a keto-compound (shown as IV below) due to keto-enol tautomerism of the 3-hydroxy cephem compound and most of the examples in the patents by Scartazzini et al. are limited to benzhydryl esters only. The application of 3-hydroxy cephem benzhydryl ester is limited. Further, the formation and characterization of Z- and E-rotamers of 3-hydroxy cephem derivatives have never been visualized or experienced earlier.

SUMMARY OF THE INVENTION

In accordance with the present invention, the previously unknown Z- and E-rotamers of 3-hydroxy cephem derivatives have been produced, isolated, and characterized. The Z- and E-rotamers of 4-hydroxy cepham derivatives may be visualized as follows:

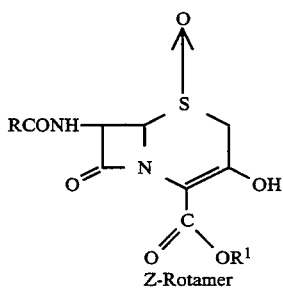

Z-Rotamer (II)

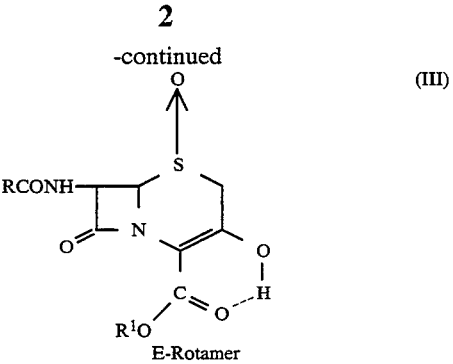

E-Rotamer (III)

In the present invention, the 3-hydroxy cephem derivative which has a non-hydrogen bonded 3-hydroxy group has been assigned Z-rotamer configuration, whereas the 3-hydroxy cephem derivative which has a hydrogen bond between the 3-hydroxy group and the carbonyl of the 4-ester group has been assigned E-rotamer configuration.

Z- and E-rotamers differ significantly in chemical and physical properties. E-rotamer is thermodynamically more stable. In view of the greater thermodynamic stability and higher solubility of E-rotamer in organic solvents, it offers several advantages over the Z-rotamer when produced and used in subsequent synthetic steps on commercial scale.

The present invention also relates to a novel process for the manufacture of Z- and E-rotamers of 7-acylamino-3-hydroxycephem-4-carboxylate-1-oxide (II and III) from 7-acylamino-3-exomethylenecepham-4-carboxylate-1-oxide (I). The process of this invention is practiced by treating 3-exomethylene cepham derivatives with ozone. Z-rotamer is isolated by filtering the solid after ozonolysis in an inert organic solvent in the presence of an organic acid and subsequent decomposition of the ozonide. E-rotamer is obtained exclusively by the addition of some inorganic or organic base during ozonolysis in an inert organic solvent and removal of the solvent at low temperature. Z-rotamer when dissolved in an organic solvent or heated in an organic solvent or treated with a base gives E-rotamer. The formation of Z- or E-rotamers depends on the pH of the reaction medium, the polarity of the organic solvents used in ozonolysis, and the size of the protecting group used in esterification at position-4. Due to strong hydrogen bonding between the 3-hydroxy group and the carbonyl group of the 4-ester group, E-rotamer would never exhibit keto-enol tautomerism.

The manufacturing process for the Z- and E-rotamers (II and III) is outlined below.

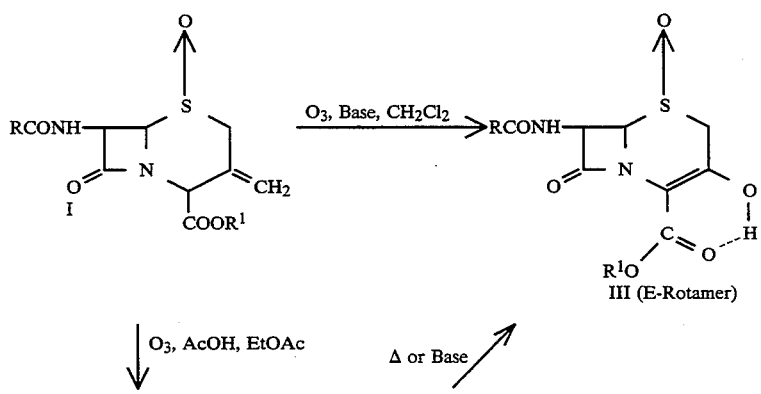

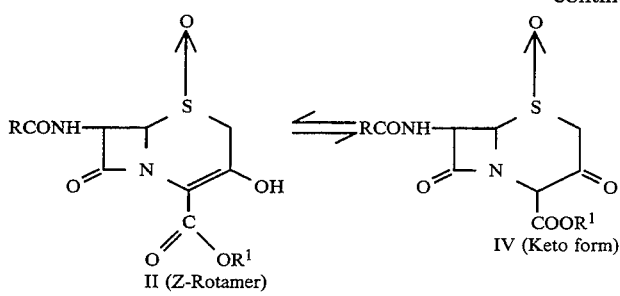

II (Z-Rotamer)    IV (Keto form)

DETAILED DESCRIPTION

According to the present invention, 3-exomethylene cepham-4-carboxylate-1-oxide (I) is subjected to ozonolysis under varying pH conditions and inert organic solvents of varying polarity as follows: (a) ozonolysis in an inert organic solvent in the presence of a base at a temperature of about −80° C. to 20° C. provides E-rotamer (III) of 3-hydroxy-cephem derivative, (b) ozonolysis in an inert organic solvent in the presence of acetic acid at −80° C. to +20° C. provides Z-rotamer (II) of 3-hydroxy cephem derivative, and (c) ozonolysis in an inert organic solvent at −80° C. to +20° C. without acid or base gives a mixture of Z- and E-rotamers of 3-hydroxy cephem derivatives. Z-rotamer being insoluble in most of the organic solvents is filtered out and E-rotamer is recovered from the mother liquor after concentration at a lower temperature.

Z-rotamer of 3-hydroxy cephem derivative (II) on heating or dissolving in an organic solvent or treatment with an organic base or inorganic base gives E-rotamer (III) which is thermodynamically more stable. All attempts to convert E-rotamer to Z-rotamer have failed.

In the formulae (II) and (III), R is an amino protecting group such as aryl, aralkyl, or aryloxyalkyl, such as phenoxy lower alkyl, phenyl lower alkyl, thienyl lower alkyl, etc., and $R^1$ is linear or branched chain alkyl, aryl, aralkyl, aryloxyalkyl, or aroxyalkyl, such as benzyl, p-methoxybenzyl, p-nitrobenzyl, diphenylmethyl, etc.

Solvents which can be employed in the present process are those solvents which are inert to oxidation by ozone. Suitable solvents in the present process include, for example, methylene chloride, chloroform, ethylene chloride, 1,1,2-trichloroethane, acetonitrile, propionitrile, methyl acetate and ethyl acetate. The most preferred solvent in the process is methylene chloride for E-rotamer and ethyl acetate for Z-rotamer.

The temperature range which can be used in the process of this invention is about −80° C. to about +20° C. The preferred temperature is between −40° C. to +10° C.

The organic bases which can be used in the above process for the production of E-rotamer (III) are, for example, pyridine, triethylamine, dimethylaniline, quinoline, etc., whereas inorganic bases which could be employed are, for example, sodium bicarbonate, potassium bicarbonate, potassium carbonate, sodium carbonate, etc.

Figure 1:
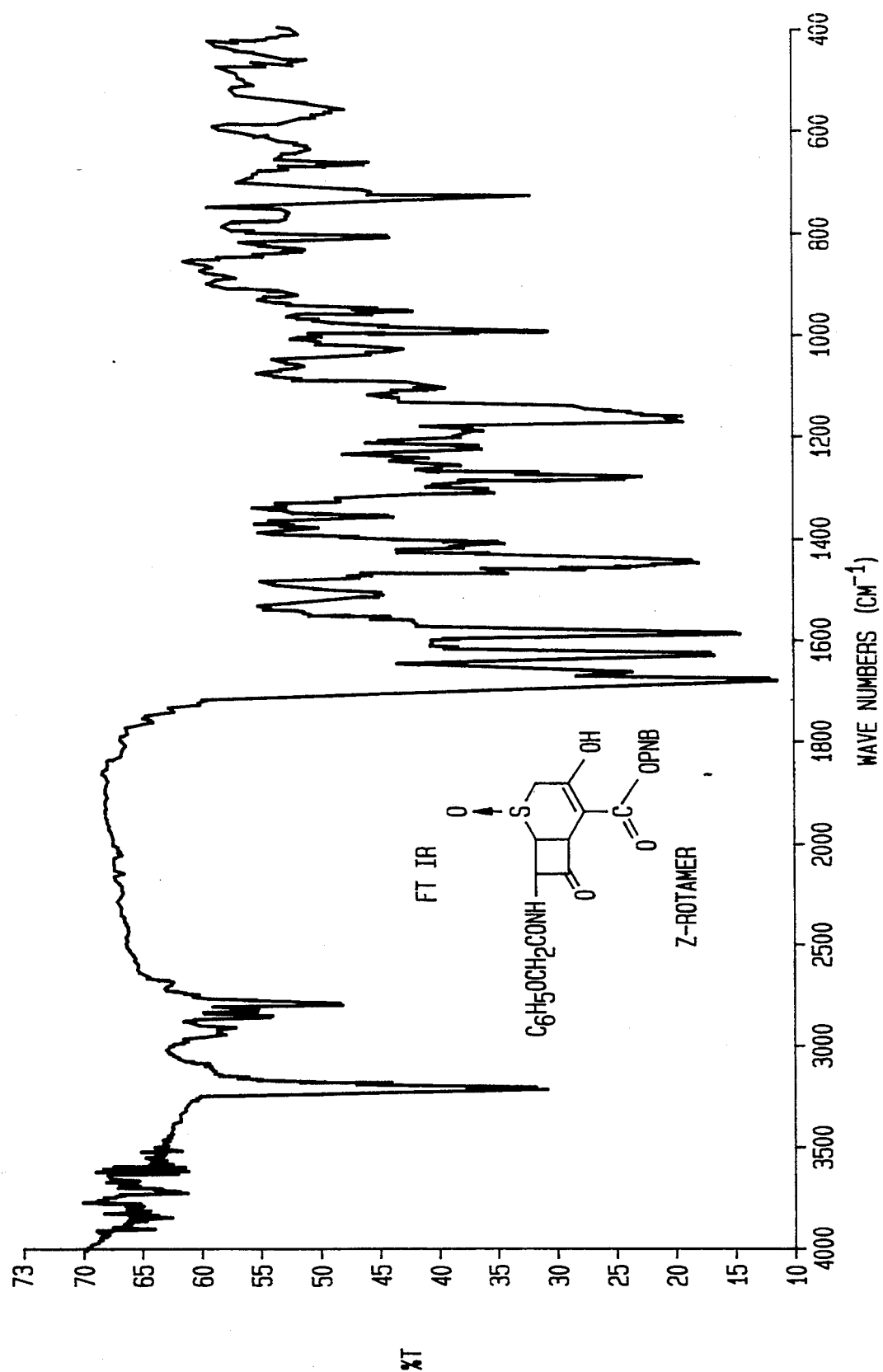
FIG. 1 shows the IR spectrum of the Z-rotamer of p-nitrobenzyl-7-phenoxyacetamido-3-hydroxy-cephem-4-carboxylate-1-oxide.
Figure 2:
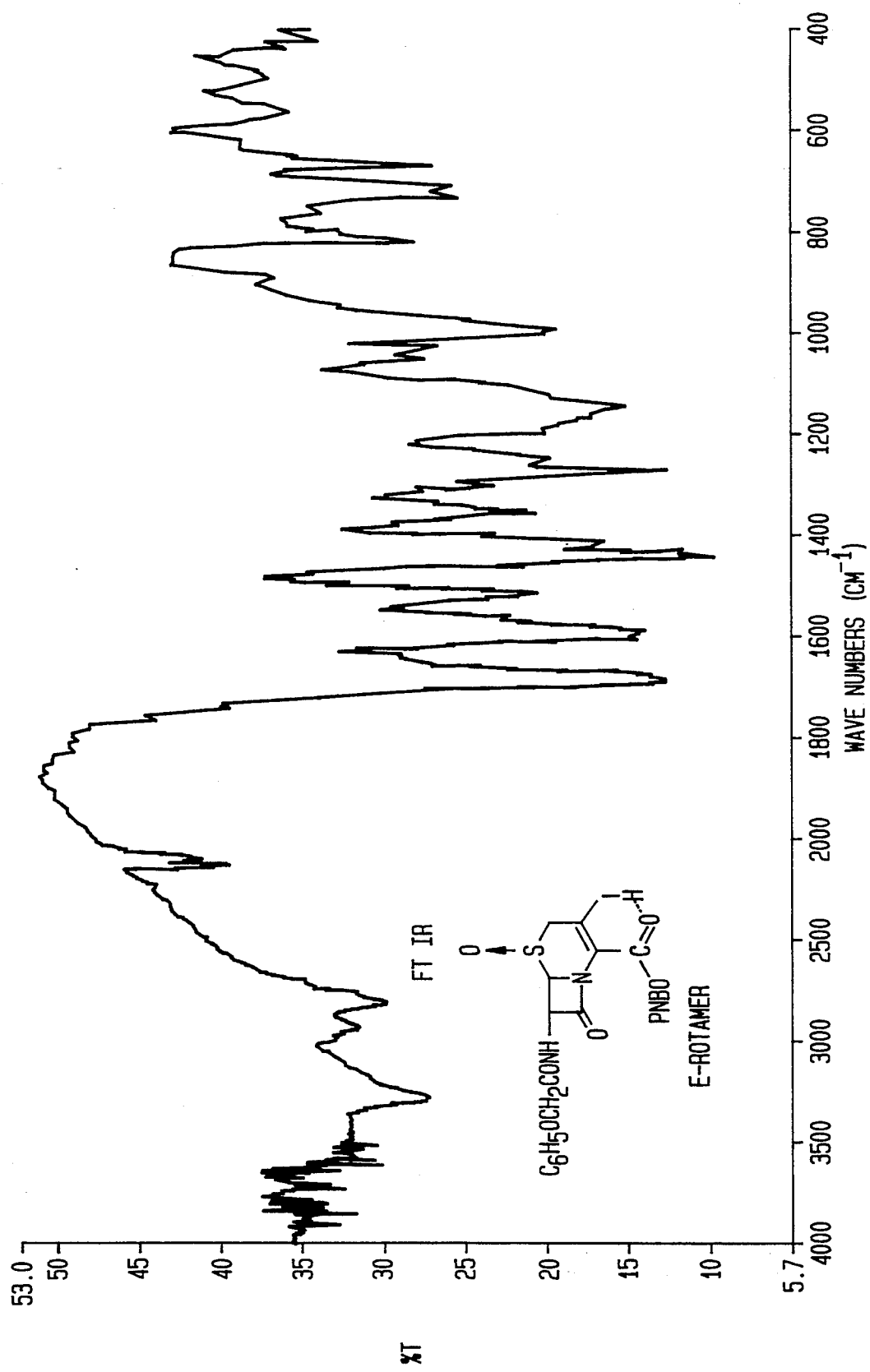
FIG. 2 shows the IR spectrum of the E-rotamer of p-nitrobenzyl-7-phenoxyacetamido-3-hydroxy-cephem-4-carboxylate-1-oxide.
Figure 3:
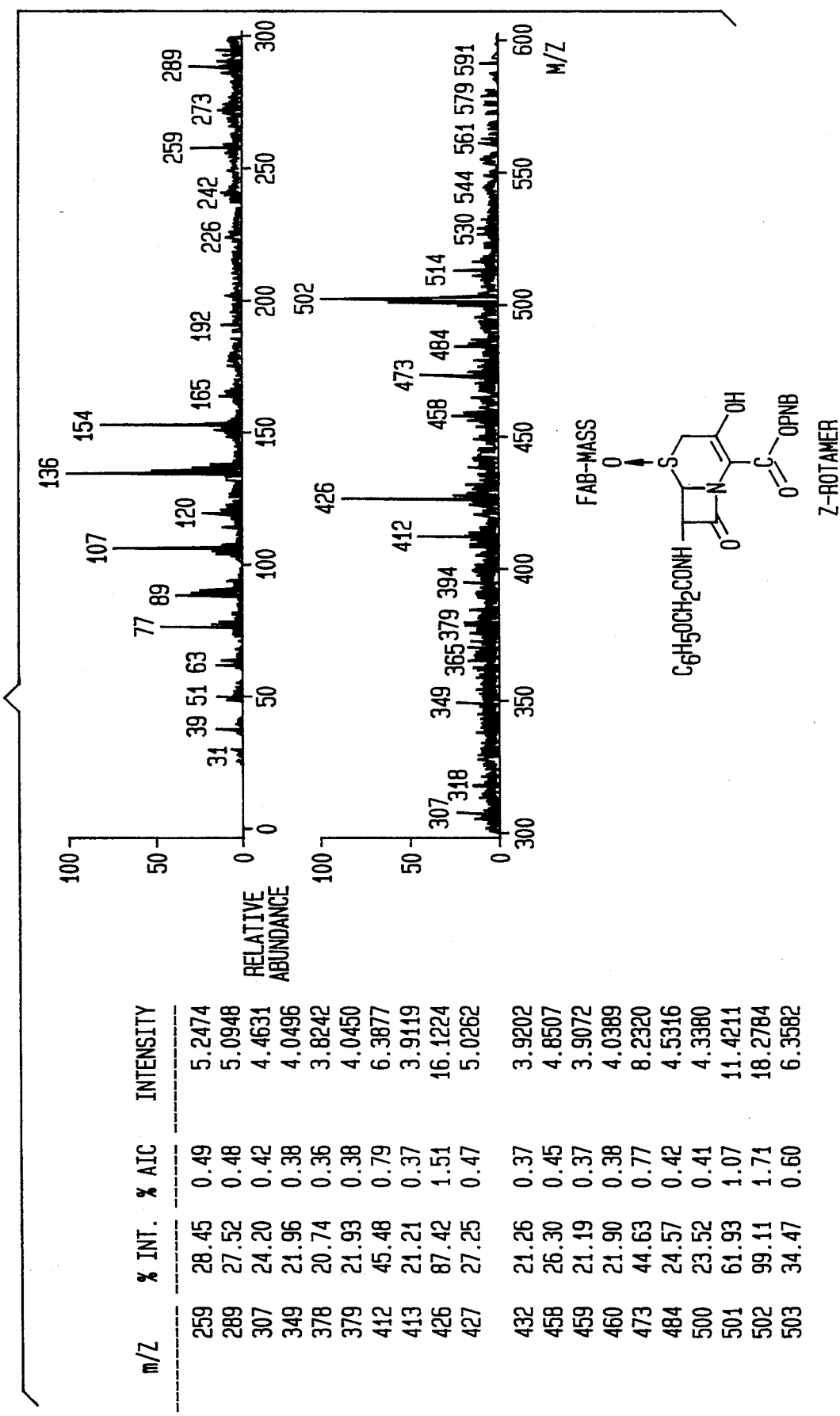
FIG. 3 shows the mass spectrum of the Z-rotamer of p-nitrobenzyl-7-phenoxyacetamido-3-hydroxy-cephem-4-carboxylate-1-oxide.
Figure 4:
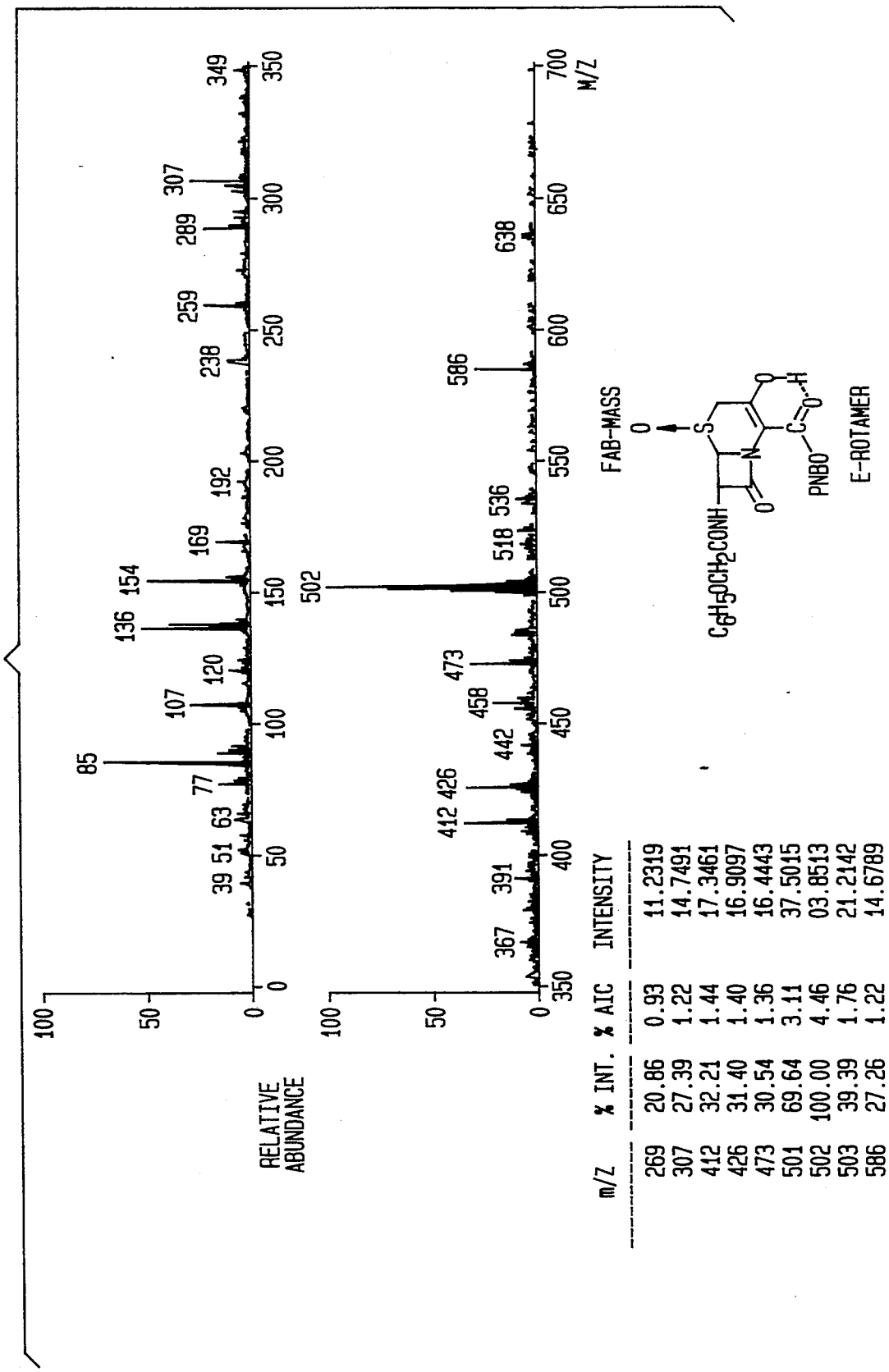
FIG. 4 shows the mass spectrum of the E-rotamer of p-nitrobenzyl-7-phenoxyacetamido-3-hydroxy-cephem-4-carboxylate-1-oxide.

Z-rotamer (II) and E-rotamer (III) differ in chemical/physical properties such as melting point, solubility, chemical reactivity, IR and mass spectra. As shown in FIG. 1, in the IR spectrum of Z-rotamer of p-nitrobenzyl-7-phenoxyacetamido-3-hydroxycephem-4-carboxylate-1-oxide, a sharp signal of the 3-hydroxy group appears at about 3300 $cm^{-1}$, and a signal for 3-keto appears at 1755 $cm^{-1}$. In the IR spectrum of the corresponding E-rotamer (FIG. 2), the 3-hydroxy signal is very weak and the 3-keto signal is not present due to the hydrogen bonding with the carbonyl of the 4-ester group. Also, in the case of Z-rotamer, the carbonyl of the 4-ester group appears at 1717 $cm^{-1}$. In E-rotamer, the carbonyl of the 4-ester group is shifted towards lower wave number and appears at about 1690 $cm^{-1}$ due to hydrogen bonding between the carbonyl of the 4-ester group and the 3-hydroxy group. In mass spectra of both rotamers (see FIGS. 3 and 4), there is a marked difference in the intensities of the peaks.

Z-rotamer (II) possesses a non-bonded 3-hydroxy group and hence exhibits keto-enol tautomerism, whereas in E-rotamer (III) the 3-hydroxy group is strongly hydrogen bonded with the carbonyl of the 4-ester group and does not exhibit keto-enol tautomerism. Since these is a free rotation of the carboxylate group about the single bond to the $C_4$-carbon

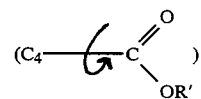

Z-rotamer, would tend to transform into the more stable configuration, i.e., into E-rotamer when dissolved in organic solvents. Hence, when Z-rotamer (II) is dissolved in an organic solvent such as DMSO or DMF and re-precipitated back, it provides E-rotamer (III).

The physical and chemical properties of Z- and E-rotamers of p-nitrobenzyl-7-phenoxyacetamido-3-hydroxy-cephem carboxylate-1-oxide are summarized in the following table.

| PHYSICAL AND CHEMICAL PROPERTIES OF Z- AND E-ROTAMER OF p-NITROBENZYL-7-PHENOXYACETA-MIDO-3-HYDROXY CEPHEM-4-CARBOXYLATE-1-OXIDE | | |
|---|---|---|
| PROPERTIES | Z-ROTAMER | E-ROTAMER |
| Description | White crystalline powder | White crystalline powder |
| Melting point | 163–165° C. | 110–115° C. |
| Solubility in Organic Solvents | Insoluble in EtOAc, $CH_2Cl_2$, $CHCl_3$ etc. | Soluble in $CHCl_3$, $CH_2Cl_2$, etc. |
| On Heating in Organic Solvents ($CH_2Cl_2$/MeOH) | Gives E-rotamer | Remains unchanged |
| Reaction with Inorganic or Organic Base | Gives E-rotamer | Remains unchanged |
| Chemical reactivity towards triphenyl phosphite.$Cl_2$ complex | Gives p-nitrobenzyl-7-amino-3-chloro-cephem-4-carboxylate | Gives p-nitrobenzyl-7-phenoxy-acetamido-3-chloro-cephem-4-carboxylate |
| IR (KBr) | 3300,1770,1755,1710, 1680,1600,1525,1350, 1220,1030,835,750, 680 $cm^{-1}$ | 1780,1690,1680,1600, 1520,1380,1200,1040, 850,750,735,690 $cm^{-1}$ |
| FAB MASS M/Z (% INT) | 289(27.62),307(24.20), 412(45.48),426(87.42), 426(87.42),473(44.63), 501(61.93),502(99.11) | 289(20.86),307(27.39), 412(32.21),426(31.40), 473(30.54),501(69.64), 502(100%). |

The invention will now be described by reference to the following examples.

EXAMPLE 1

Z-ROTAMER OF P-NITROBENZYL-7-PHENOXYACETAMIDO-3-HYDROXYCEPHEM-4-CARBOXYLATE-1-OXIDE p-Nitrobenzyl-7-phenoxyacetamido-3-exomethylenecepham-4-carboxylate-1-oxide (10 g) was dissolved in $CH_2Cl_2$ (120 ml). Ozone gas was bubbled into this solution at −20° C. to −30° C. After completion of the reaction, the mixture was stirred for 1 hour at −20° C. and 1 hour at 20° C. The solid thus separated was filtered and dried. Yield 7 g, m.p. 163°–165° C.

IR(KBR) in $cm^{-1}$: 3300 (OH), 1770 (β-lactam carbonyl), 1755 (3-carbonyl), 1710 (4-ester carbonyl), 1680 (7-amide carbonyl).

EXAMPLE 2

E-ROTAMER OF p-NITROBENZYL-7-PHENOXYACETAMIDO-3-HYDROXYCEPHEM-4-CARBOXYLATE-1-OXIDE p-Nitrobenzyl-7-phenoxyacetamido-3-exomethylenecepham-4-carboxylate-1-oxide (10 g) was dissolved in $CH_2Cl2$ (120 ml). $K_2CO_3$ (400 mg) was added and the solution was cooled to −20° C. to −30° C. Ozone gas was passed into the solution. The completion of the reaction was checked by TLC. The reaction mixture was further stirred for 1 hour at −20° C. and then allowed to warm up to 20°–25° C. and stirred for 3 hours. The almost clear solution was filtered to remove $K_2CO_3$. The filtrate was concentrated below 40° C. under vacuum. The residue on trituration with hexane gave a crystalline solid which was filtered and dried. Yield 9.2 g, m.p. 108°–112° C.

IR(KBR) in $cm^{-1}$: 1780 (β-lactam carbonyl), 1690 (4-ester carbonyl), 1680 (7-amide carbonyl).

EXAMPLE 3 p-Nitrobenzyl-7-phenoxyacetamido-3-exomethylenecepham-4-carboxylate-1-oxide (10 g) was dissolved in $CH_2Cl_2$ (120 ml). The solution was cooled to −20° to −30° C. A stream of ozone was passed into the solution until the reaction was complete. Triethylamine (200 mg) was added. The mixture was stirred for 1 hour at −20° C. and then was allowed to warm up to room temperature (20° to 30° C.). The clear solution thus obtained was concentrated. The residue was triturated with hexane. The solid thus obtained was filtered and dried to give E-rotamer of 3-hydroxycephem compound. Yield 8.0 g.

IR(KBR) in $cm^{-1}$: 1780 (β-lactam carbonyl), 1690 (4-ester carbonyl), 1680 (7-amide carbonyl).

EXAMPLE 4

10 g of p-nitrobenzyl-7-phenoxyacetamido-3-exomethylenecepham-4-carboxylate-1-oxide was suspended in $CH_2Cl_2$ (120 ml). $KHCO_3$ (400 mg) was added and ozone passed at −20° to −30° C. The reaction mixture was worked up as described in Example 2. Yield 9.3 g, m.p. 108°–110° C.

IR(KBR) in $cm^{-1}$: 1780 (β-lactam), 1690 (4-ester carbonyl), 1680 (7-amide carbonyl).

EXAMPLE 5

10 g of p-nitrobenzyl-7-phenoxyacetamido-3-exomethylenecepham-4-carboxylate-1-oxide was suspended in $CH_2Cl_2$ (120 ml) and ozone was passed through at −20° to −30° C. After the completion of reaction, dimethylaniline (200 mg) was added, stirred for 1 hour at −20° C. and then allowed to warm up to 30° C. The solution became clear and worked up as described in Example 3. Yield 8.5 g.

IR identical with compound obtained in Example 3.

EXAMPLE 6

E-ROTAMER OF DIPHENYLMETHYL-7-PHENOXYACETAMIDO-3-HYDROXYCEPHEM-4-CARBOXYLATE

Through a solution of 2 g of diphenylmethyl-7-phenoxyacetamido-3-exomethylene-cepham-4-carboxylate-1-oxide in $CH_2Cl_2$ (40 ml) at −20° C., a stream of ozone was passed until the reaction was complete on TLC (7 min.). The temperature of the reaction mixture was then raised to 25°–30° C. and stirred for 1.5 hours. The clear solution thus obtained was concentrated and the residue was stirred with hexane (15 ml) for 20 minutes. The solid thus obtained was filtered, washed with hexane and dried. Yield 2 g, m.p. 89°–95° C.

IR(KBr) in $cm^{-1}$: 1780 (β-lactam carbonyl), 1680 (4-ester carbonyl), 1665 (7-amide carbonyl).

EXAMPLE 7

Z AND E-ROTAMERS OF p-NITROBENZYL-7-PHENOXYACETAMIDO-3-HYDROXYCEPHEM-4-CARBOXYLATE-1-OXIDE

Through a solution of 10 g of p-nitrobenzyl-7-phenoxyacetamido-3-exomethylene-cepham-4-carboxylate-1oxide in 150 ml of methylene chloride and 1 ml of methanol at −30° C., a stream of ozone was passed for 25 minutes. The reaction mixture was treated with 30 g of sodium bisulphite and was stirred for 1 hour at 0° C.

100 ml water was added to the above reaction mixture and was further stirred for 30 minutes at +10° C. The solid obtained was filtered, washed with 3×25 ml water and finally with 2×25 ml ethyl acetate, and then dried at 45° C. for 3 hours under vacuum. Yield 5.6 g, m.p. 158°–159° C.

IR was identical with Z-rotamer described in Example 1. Mother liquor was evaporated under reduced pressure and the volume was reduced to half. The residue (70 ml) was stirred for 2 hours in 140 ml hexane. The solid material was filtered, washed with 10 ml hexane and dried at 45° C. for 3 hours under vacuum. Yield 2.5 g, m.p. 110°–112° C. IR was identical with E-rotamer described in Example 2.

EXAMPLE 8

Z-ROTAMER OF P-NITROBENZYL-7-PHENYLACETAMIDO-3-HYDROXYCEPHEM-4-CARBOXYLATE-1-OXIDE

Through a solution of 2 g of p-nitrobenzyl-7-phenylacetamido-3-exomethylene-cepham-4-carboxylate-1-oxide in 50 ml of methylene chloride at −20° C., a stream of ozone was passed until the completion of the reaction (10 minutes). The temperature of the reaction mixture was increased to 30°–32° C. and stirred for 1.5 hours. The solid was filtered and dried at 35°–40° C. under vacuum for 2 hours. Yield 1.3 g (64.5%), m.p. 175°–183° C.

IR(KBr) in cm$^{-1}$: 1780 ($\beta$-lactam carbonyl), 1720 (4-ester carbonyl), 1660 (7-amide carbonyl).

EXAMPLE 9

CONVERSION OF Z-ROTAMER TO E-ROTAMER OF p-NITROBENZYL-7-PHENOXYACETAMIDO-3-HYDROXYCEPHEM-4-CARBOXYLATE-1-OXIDE 1 g of p-nitrobenzyl-7-phenoxyacetamido-3-hydroxy cephem-4-carboxylate-1-oxide (Z-rotamer) was dissolved in 9 ml of DMSO at room temperature. It was then precipitated by adding 25 ml of water under stirring. The product thus separated was filtered, washed thoroughly with water and finally with methanol, and then dried at 40°–45° C. under vacuum for 3 hours. Yield 0.85 g, m.p. 110°–115° C.

IR(KBr) in cm$^{-1}$: 1780 ($\beta$-lactam carbonyl), 1690 (4-ester carbonyl), 1680 (7-amide carbonyl).

EXAMPLE 10

CONVERSION OF Z-ROTAMER TO E-ROTAMER OF p-NITROBENZYL-7-PHENOXYACETAMIDO-3-HYDROXYCEPHEM-4-CARBOXYLATE-1-OXIDE 2 g of p-nitrobenzyl-7-phenoxyacetamido-3-hydroxy cephem-4-carboxylate-1-oxide (Z-rotamer) was refluxed in a mixture of 20 ml chloroform and 3–4 drops of methanol for 6 hours and then evaporated under reduced pressure until dryness. Yield 1.72 g, m.p. 112°–116° C.

IR(KBR) in cm$^{-1}$: 1780 ($\beta$-lactam carbonyl), 1690 (4-ester carbonyl), 1680 (7-amide carbonyl).

EXAMPLE 11

CONVERSION OF Z-ROTAMER TO E-ROTAMER OF p-NITROBENZYL-7-PHENYLACETAMIDO-3-HYDROXYCEPHEM-4-CARBOXYLATE-1-OXIDE 400 mg of p-nitrobenzyl-7-phenylacetamido-3-hydroxycephem-4-carboxylate-1-oxide (Z-rotamer) in 5 ml of CH$_2$Cl$_2$ was treated with 1 drop of triethylamine at −10° C. The reaction mixture was stirred for 40 minutes and the clear solution thus obtained was evaporated under reduced pressure. Residue was stirred with 10 ml of hexane for 15 minutes and solid was filtered, washed with 2 ml of hexane and dried, and then purified with hexane/CH$_2$Cl$_2$. Yield 400 mg, m.p. 130°–135° C.

IR(KBr) in cm$^{-1}$; 1781 ($\beta$-lactam carbonyl), 1654 (4-ester carbonyl and 7-amide carbonyl.

EXAMPLE 12

CONVERSION OF Z-ROTAMER TO E-ROTAMER OF p-NITROBENZYL-7-PHENOXYACETAMIDO-3-HYDROXYCEPHEM-4-CARBOXYLATE-1-OXIDE 2 g of p-nitrobenzyl-7-phenoxyacetamido-3-hydroxycephem-4-carboxylate-1-oxide (Z-rotamer) was stirred in a mixture of 40 ml of methylene chloride and 45 mg of N,N-dimethylaniline at 30°–32° C. for 2.5 hours. Reaction mixture was then filtered, the filtrate was evaporated under reduced pressure and the residue was stirred with 15 ml of hexane for 30 minutes. The solid was filtered, washed with 5 ml of hexane and dried. Yield 1.3 g, m.p. 110°–115° C.

IR(KBr) in cm$^{-1}$: 1780 ($\beta$-lactam carbonyl), 1690 (4-ester carbonyl), 1680 (7-amide carbonyl).

EXAMPLE 13

Z-ROTAMER OF DIPHENYLMETHYL-7-PHENYLACETAMIDO-3-HYDROXYCEPHEM-4-CARBOXYLATE-1-OXIDE

Through a suspension of diphenylmethyl-7-phenylacetamido-3-exomethylenecepham-4-carboxylate-1-oxide (10 g) in a mixture of ethyl acetate (200 ml) and acetic acid (5 ml) at −25° C., a stream of ozone was passed until the reaction was complete. The excess of ozone was expelled with N$_2$. Dimethylsulfide (1.78 g) was added and the resulting suspension was stirred at 0° C. for 0.5 hours. The suspension was cooled to −10° C., filtered and the solid was washed with chilled ethyl acetate (20 ml) and dried. Z-rotamer of diphenylmethyl-7-phenylacetamido-3-hydroxycephem-4-carboxylate-1-oxide was obtained as a white (4-ester carbonyl), 1650 (7-amide carbonyl).

EXAMPLE 14

CONVERSION OF Z-ROTAMER TO E-ROTAMER OF DIPHENYLMETHYL-7-PHENOXYACETAMIDO-3-HYDROXY-CEPHEM-4-CARBOXYLATE-1-OXIDE 2 g of diphenylmethyl-7-phenoxyacetamido-3-hydroxy-cephem-4-carboxylate-1-oxide (Z-rotamer) was suspended in 100 ml of chloroform, followed by the addition of 2 ml of methanol. The reaction mixture was refluxed for one hour. Clear solution thus obtained was evaporated under reduced pressure. Yield 1.8 g (90%), m.p. 105°–110° C.

KR (KBr) cm$^{-1}$: 1786 ($\beta$-lactam carbonyl), 1684 (4-ester carbonyl), 1676 (7-amide carbonyl).

EXAMPLE 15

Z-ROTAMER OF p-NITROBENZYL-7-PHENOXYACETAMIDO-3-HYDROXYCEPHEM-4-CARBOXYLATE-1-OXIDE

Through a suspension of 10 g of p-nitrobenzyl-7-phenoxyacetamido-3-exomethylenecephem-4-carboxylate-1-oxide in 200 ml of ethyl acetate and 5 ml acetic acid, a stream of ozone was passed at −18° C. for 25 minutes. After completion of the reaction, 1.6 ml of dimethyl sulfide was added. The temperature was raised to 0°–5° C. and the mixture was stirred for 2 hours at this temperature. The solid was filtered, washed with ethyl acetate and dried. Yield 18.6 g, m.p. 163°–165° C.

IR(KBr) in cm$^{-1}$: 3300 (OH), 1770 ($\beta$-lactam carbonyl), 1755 (3-carbonyl), 1710 (4-ester carbonyl), 1680 (7-amide carbonyl).

While the invention has been described by reference to specific embodiments, this was for purposes of illustration only. Numerous alternative embodiments will be apparent to those skilled in the art and are considered to be within the scope of the invention.

We claim:

1. A process for the manufacture and isolation of an E-rotamer of 7-acylamino-3-hydroxy-cephem-4-carboxylate-1-oxide having the formula:

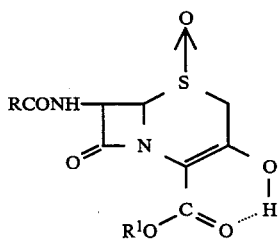

wherein R is aryl, aralkyl, or aryloxyalkyl, and R' is linear or branched chain alkyl, aryl, aralkyl, aryloxyalkyl, or alkoxyalkyl, comprising reacting in an inert organic solvent a 7-acylamino-3-exomethylenecephem-4-carboxylate-1-oxide of the formula:

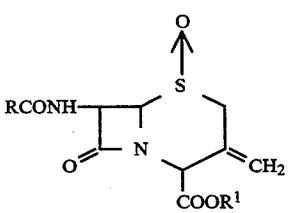

wherein R and R' are defined as above, with ozone in the presence of a catalytic amount of base at a temperature ranging from about −80° C. to about +20° C., removing any solids from said solvent, and recovering said E-rotamer from said remaining solvent.

2. The process of claim 1 wherein R is phenyl lower alkyl, phenoxy lower alkyl, or thienyl lower alkyl.

3. The process of claim 1 wherein R$^1$ is benzyl, p-methoxybenzyl, p-nitrobenzyl, or diphenylmethyl.

4. The process of claim 1 wherein said solvent is a halogenated hydrocarbon, a nitrile, or an ester.

5. The process of claim 4 wherein said solvent is methylene chloride, ethylene chloride, 1,1,2-trichloroethane, chloroform, acetonitrile, propionitrile, methyl acetate, or ethyl acetate.

6. The process of claim 1 wherein said base is an organic base.

7. The process of claim 6 wherein said organic base is dimethyl aniline, pyridine, triethyl amine, or N-benzyl diethylamine.

8. The process of claim 1 wherein said base is an inorganic base.

9. The process of claim 8 wherein said inorganic base is sodium carbonate, potassium carbonate, sodium bicarbonate, or potassium carbonate.

10. The process of claim 1 wherein said temperature ranges from about −40° C. to about +5° C.

11. The process of claim 1 wherein said temperature ranges from about −40° C. to about −10° C.

12. The process of claim 1 wherein R is phenyxymethyl and R$^1$ is p-nitrobenzyl.

13. A process for converting a Z-rotamer of 7-acylamino-3-hydroxy-cephem-4-carboxylate-1-oxide having the formula:

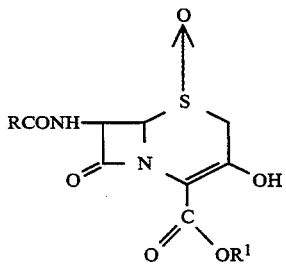

wherein R is aryl, aralkyl, or alkoxyalkyl, and R$^1$ is linear or branched chain alkyl, aryl, aralkyl, aryloxyalkyl, or alkoxyalkyl, into an E-rotamer of 7-acylamino-4-hydroxy-cephem-4-carboxylate-1-oxide having the formula:

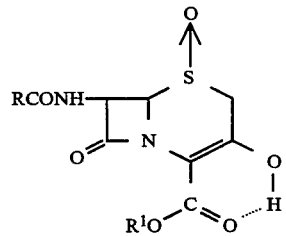

wherein R and R$^1$ are as defined above, comprising dissolving said Z-rotamer in an organic solvent and recovering said E-rotamer from said solvent.

14. The process of claim 13 wherein R$^1$ is benzyl, p-methoxybenzyl, p-nitrobenzyl, or diphenyl methyl.

15. The process of claim 13 wherein R is phenyl lower alkyl, phenoxy lower alkyl, or thienyl lower alkyl.

16. The process of claim 13 wherein said organic solvent is dimethyl sulfoxide, chloroform, methanol, dichloromethane, methanol, or mixtures thereof.

17. The process of claim 1 wherein said solids are removed from said solvent by filtering said solvent.

18. The process of claim 1 wherein said solids comprise the Z-rotamer of 7-acylamino-3-hydroxy-cephem-4-carboxylate-1-oxide.

* * * * *